(12) United States Patent
Hintzer et al.

(10) Patent No.: US 8,344,190 B2
(45) Date of Patent: Jan. 1, 2013

(54) PROCESS OF MAKING FLUOROOLEFINS BY THERMAL DECOMPOSITION OF FLUORINATED MATERIALS

(75) Inventors: Klaus Hintzer, Kastl (DE); Gunther J. Kaempf, Altoetting (DE); Thomas Kolbeck, Burgkirchen (DE); Tilman C. Zipplies, Burghausen (DE); Monika A. Willert-Porada, Bayreuth (DE); Thorsten Gerdes, Eckersdorf (DE); Achim Schmidt-Rodenkirchen, Bayreuth (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/121,297

(22) PCT Filed: Sep. 30, 2009

(86) PCT No.: PCT/US2009/059011
§ 371 (c)(1),
(2), (4) Date: Mar. 28, 2011

(87) PCT Pub. No.: WO2010/039820
PCT Pub. Date: Apr. 8, 2010

(65) Prior Publication Data
US 2011/0184214 A1    Jul. 28, 2011

(30) Foreign Application Priority Data

Oct. 1, 2008  (GB) .................................. 0817873.3

(51) Int. Cl.
*C07C 21/18* (2006.01)
(52) U.S. Cl. ........................ 570/136; 528/480; 528/481
(58) Field of Classification Search ........................ None
See application file for complete search history.

(56) References Cited

U.S. PATENT DOCUMENTS

| 2,519,983 | A |   | 8/1950  | Simons |
| 3,832,411 | A |   | 8/1974  | Arkles et al. |
| 5,322,597 | A |   | 6/1994  | Childs et al. |
| 5,432,259 | A | * | 7/1995  | Schottle et al. ............... 528/481 |
| 6,160,031 | A | * | 12/2000 | Poree et al. ................... 522/153 |
| 6,797,913 | B2 |   | 9/2004  | Van Der Walt |
| 2004/0112758 | A1 | * | 6/2004 | Bauer et al. ................... 205/619 |

FOREIGN PATENT DOCUMENTS

| EP | 1 481 957      | 12/2004 |
| WO | WO 98/04599    | 2/1998  |
| WO | WO 98/50603    | 11/1998 |
| WO | WO 01/58840    | 8/2001  |
| WO | WO 2007/063462 | 6/2007  |

\* cited by examiner

*Primary Examiner* — Sudhakar Katakam
(74) *Attorney, Agent, or Firm* — C. Michael Geise

(57) ABSTRACT

Process for producing fluorinated olefins from fluorinated materials, the process comprising thermally decomposing the fluoropolymers into fluoroolefins in a reactor having a feeding zone where the fluorinated materials are fed into the reactor and a decomposition zone where the fluorinated materials are thermally decomposed and wherein the thermal decomposition is carried out in the presence of microwave irradiation.

9 Claims, No Drawings

PROCESS OF MAKING FLUOROOLEFINS BY THERMAL DECOMPOSITION OF FLUORINATED MATERIALS

CROSS REFERENCE TO RELATED APPLICATIONS

This application is a national stage filing under 35 U.S.C. 371 of PCT/US2009/059011, filed Sep. 20, 2009, which claims priority to Great Britain Application No. 0817873.3, filed Oct. 1, 2008, the disclosure of which is incorporated by reference in its/their entirety herein.

FIELD

The following disclosure relates to processes for generating fluoroolefines, in particular, tetrafluoroethylene, by thermal decomposition of fluorinated materials.

BACKGROUND

Fluorinated olefins, in particular tetrafluoroethylene (TFE), are important raw materials for the preparation of fluoropolymers. TFE is commonly prepared from fluorine and chlorine containing starting materials (e.g. R22=$CHClF_2$), which are of environmental concern, for example for their potential effect on ozone depletion in the atmosphere. Therefore, there exists a need for alternative ways of producing TFE.

TFE and other fluoroolefins are known to be derivable from thermal decomposition (pyrolysis) of fluoropolymers, such as polytetrafluoroethylene.

Fluoropolymers, i.e. polymers having a fluorinated backbone, have been used in a variety of applications because of several desirable properties such as heat resistance, weatherability, UV-stability and resistance to harsh chemical environments and have found widespread application as starting materials for household and chemical appliances, such as for example coatings for cookware, as raw material for making O-rings, hoses or sealings for example of fuel systems, or as textures in the building industries. Various fluoropolymers and their applications are, for example, described in "Modern Fluoropolymers", edited by John Scheirs, Wiley Science 1997, "Fluoropolymer Applications in Chemical Processing Industries, edited by Sina Ebnesajjad and Pradip Khaladkar, William Andrew Inc, Norwich, N.J., USA, 2005.

Several technologies for pyrolysing fluoropolymers have been described, for example pyrolysis by steam (U.S. Pat. No. 3,832,411 to Arkles et al), by radio frequencies (U.S. Pat. No. 6,797,913 to van der Walt et al) or by electric arcs (international patent application WO 01/58840 to van der Walt et al). These technologies, however, may lead to low conversion and/or involve high energy consumption. Furthermore, repolymerization may take place within the described processes which may lead to clogging of the equipment and increased working-up procedures. Moreover, these technologies may require elaborate equipment and complex monitoring.

Surprisingly it was found, that at least of the above-mentioned drawbacks could be overcome by pyrolysis in the presence of microwave irradiation, in particular while contacting the fluorinated material to be pyrolysed in the presence of microwave-active particles.

SUMMARY

In one aspect there is provided a process for producing fluorinated olefins from fluorinated materials, the process comprising thermally decomposing the fluorinated materials into fluoroolefins in the presence of microwave irradiation.

In a further aspect there is provided a process of generating tetrafluoroethylene comprising
(i) fluorinating hydrocarbons to generate fluorinated hydrocarbons and
(ii) subjecting the fluorinated hydrocarbons to a thermal decomposition process comprising thermally decomposing the fluorinated materials into fluoroolefins in the presence of microwave irradiation.

In yet another aspect there is provided a gaseous composition comprising TFE, HFP and microwave-active particles having a melting point of at least 400° C.

DETAILED DESCRIPTION

Before any embodiments of this disclosure are explained in detail, it is to be understood that the disclosure is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. Contrary to the use of "consisting", the use of "including," "comprising," or "having" and variations thereof herein is meant to encompass the items listed thereafter and equivalents thereof as well as additional items. The use of "a" or "an" is meant to encompass "one or more". Any numerical range recited herein includes all values from the lower value to the upper value. For example, if a concentration range is stated as 1% to 50%, it is intended that values such as 2% to 40%, 10% to 30%, or 1.5% to 3.9%, etc., are expressly enumerated. These are only examples of what is specifically intended, and all possible combinations of numerical values between and including the lowest value and the highest value enumerated are to be considered to be expressly stated in this application.

The processes described herein provide a way to generate fluorinated olefins, in particular, TFE and/or HFP, from fluorinated materials.

The processes described herein comprise subjecting the fluorinated material in a reactor to microwave irradiation at a temperature where decomposition of the fluorinated materials into fluorinated olefins, in particular TFE, takes place.

Fluorinated Materials:

Fluorinated materials as referred to herein include fluoropolymers, compositions comprising fluoropolymers and fluoropolymer-containing articles.

Fluorinated materials also include gaseous or liquid fluorine-containing low molecular weight compounds, such as for example by-products from the electrochemical fluorination of alkanes.

Fluorinated Organic Compounds of Low Molecular Weight:

Fluorinated organic compounds of low molecular weight have a molecular weight of less than about 1,000 g/mol. They may be liquid or gaseous at room temperature (25° C.). The compounds contain fluorine and carbon but are not limited thereto and may, for example also contain hydrogen, nitrogen, chlorine and/or bromine. Preferably, the compounds have a (molar) fluorine ratio of at least 25% more preferably at least 50%. The compounds may further include functional groups e.g. (per)fluoro alkane sulfonic, carbonic acids and their derivatives. Typical examples of fluorinated organic compounds of low molecular weight include, but are not limited to, $CF_4$, $C_2F_6$, fluorinated or polyfluorinated butanes, such as, for example fluorinated cyclobutane, R22 ($CHClF_2$), R134 ($C_2H_2F_4$), R227 ($C_3HF_7$), OIME (($CF_3$)$_2$CH—$CF_2$—O—$CH_3$) and mixtures thereof.

Typically, fluorinated organic compounds of low molecular weight or mixtures can be generated by the fluorination of carbohydrates, for example through electrochemical fluorination in electrochemical cells as for example described in U.S. Pat. No. 2,519,983, U.S. Pat. No. 5,322,597 or international patent application WO 98/50603. The feedstock for the fluorination process generally comprises linear or branched hydrocarbons or partially fluorinated hydrocarbons. A particular feedstock includes crude oil or petroleum fractions, so-called distillation cuts originating from making olefins such as ethylene or propylene. Typically, hydrocarbons or hydrocarbon containing mixtures have a boiling point below 200° C. or below 150° C. or below 100° C.

Fluoropolymers:

Fluoropolymers as referred to herein are polymers having a fluorinated backbone. The fluoropolymers may contain repeating units derived from fluorinated olefins such as, for example, tetrafluoroethylene (TFE), hexafluoropropylene (HFP), vinylidene fluoride (VDF), chlorotrifluoroethylene (CTFE), perfluorinated or partially fluorinated alkylvinyl ethers, such as for example perfluoromethylvinyl ether (PMVE), perfluoropropylvinyl ether, perfluoroisopropylvinyl ether, perfluorinated or partially fluorinated allyl ether or vinyl ether. Examples of perfluorovinyl ethers include those that correspond to the formula:

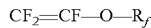

wherein $R_f$ represents a perfluorinated, linear, cyclic or branched aliphatic group that may contain one or more oxygen atoms, in particular perfluorinated vinyl ethers corresponding to the formula:

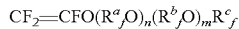

wherein $R^a_f$ and $R^b_f$ are different linear or branched or cyclic perfluoroalkylene groups of 1-6 carbon atoms, in particular 2 to 6 carbon atoms, m and n are independently 0-10 and $R^c_f$ is a perfluoroalkyl group of 1-6 carbon atoms. Specific examples of perfluorinated vinyl ethers include perfluoro(methyl vinyl)ether (PMVE), perfluoro (ethyl vinyl)ether (PEVE), perfluoro (n-propyl vinyl)ether (PPVE-1), perfluoro-2-propoxypropylvinyl ether (PPVE-2), perfluoro-3-methoxy-n-propylvinyl ether, perfluoro-2-methoxy-ethylvinyl ether and $CF_3$—($CF_2$)$_2$—O—CF($CF_3$)—$CF_2$—O—CF($CF_3$)—$CF_2$—O—CF=$CF_2$ or $CF_2$=CF—O—($CF_2$)$_3$OCF$_3$, $CF_2$=CFO($CF_2$)$_2$OCF$_3$.

Examples of perfluoroallyl ethers include those that correspond to the formula:

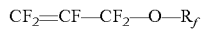

wherein $R_f$ represents a perfluorinated, linear, cyclic or branched aliphatic group that may contain one or more oxygen atoms, or in particular those corresponding to the formula: $CF_2$=CFCF$_2$O($R^a_f$O)$_n$($R^b_f$O)$_m$$R^c_f$ wherein the residues have the same meaning as described above for the corresponding vinyl ethers.

Fluorinated ionomers, (i.e. fluoropolymers containing a plurality of —$SO_3^-$, and or —$COO^-$ groups as pending and or terminal groups) may be used. Typically, such ionomers are used in the preparation of membranes in fuel cells or electrochemical processes.

The fluoropolymers may also contain repeating units derived from non-fluorinated olefins, such as $C_2$-$C_8$ olefins, for example, ethylene (E) or propylene (P).

Typical examples of fluoropolymers include, but are not limited to, homopolymers and copolymers of tetrafluoroethylene, polymers containing repeating units derived from TFE and HFP; TFE, HFP and VDF; TFE and CTFE; TFE, CTFE and E or P; TFE, E and HFP; CTFE and E or P; and combinations or blends thereof.

The fluoropolymers may be present as pure polymers, or mixtures of polymers. Compositions comprising fluoropolymers include, for example, so-called "fluoropolymer compounds", which are fluoropolymers, or polymer blends containing fluoropolymers, further containing additives such as, for example, fillers, pigments, lubricants, curing agents, curing accelerators, thermal or electrical conducting materials etc.

The fluoropolymers and the fluoropolymer-containing compositions are typically solid at room temperature (25° C.). The materials are preferably in particulate form or have been converted into particulate form, for example, by milling or grounding devices known in the art. The particles may have an average (weight average) length or diameter of from 50 μm to 100 mm or from 100 μm to 10 mm. Preferably, the particles have an average length or diameter of from about 500 μm to about 1000 μm. Preferably the particles are free-flowing.

The fluorinated materials may be pre-treated prior to subjecting them to the thermal decomposition processes described herein. Such pre-treatment may involve the separation of fluoropolymer-containing materials from non-fluoropolymer containing materials, removal of oil or dirt etc or a fluorination step, where the polymers are treated with $F_2$-gas to convert hydrogen bonds into C—F-bonds.

The fluorinated materials may be fed into the reactor in any desired manner. Particles may be preferably fed into the reactor, for example, through gravity feed. Liquids may be introduced, for example through spraying or may be vaporised into gases. Gaseous fluorinated materials may be introduced as separate gas streams, as carrier gas streams or as reaction medium.

Fluoroolefins:

Fluoroolefins include olefins corresponding to the general formula:

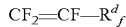

wherein $R^d_f$ represents F or a perfluoroalkyl group of 1 to 10, preferably 1 to 5 carbon atoms. Typical examples of fluoroolefins include tetrafluoroethylene (TFE) and hexafluoropropylene (HFP).

Thermal Decomposition:

The thermal decomposition of the fluorinated materials into fluorinated olefins can be carried out in any suitable reactor capable of generating the temperature required for the decomposition reaction. For example, the thermal decomposition may be carried out in rotary kilns reactors. Rotary kiln reactors are described, for example in European Pat. Appl. EP 1 481 957 to Ichida et al. The decomposition may also be carried out in extruder type reaction devices, for example devices as described in international patent application WO 2007/063462 A1 to Van der Walt et al. These devices can be operated with or without gas streams, such as for example carrier gases or gaseous reaction medium. Preferably, the decomposition is carried out in a fluidized bed reactor (see for example J. R. Howard, "Fluidized Bed Technology, Principles and Applications", Adam Hingler, New York, 1989). Typically, a gas or a gas mixture is used as fluidizing medium. The carrier gas or gaseous fluidizing or reaction medium typically comprises non-reactive gases (i.e. gases that do not react under the decomposition conditions in the reactor), such as, for example, steam, nitrogen, noble gases (Xe, Ar, Ne, He etc) and mixtures thereof. Nitrogen, noble gases and mixtures thereof are preferred. However, the carrier gas and/or medium may also contain or consist of reactive gases, i.e. fluorine-containing gases which may also decompose under the conditions in the reactor and converted into TFE and/or HFP. Carrier gas and/or reaction or fluidizing medium can be introduced in the reactor as separate gas streams. The optimum flow rates of the carrier gas or medium depends on the configuration of the reactor, the reaction and/or process conditions. Typical flow rates lie in the range of from about 0.01 to about 1,000 reactor volumes/min, preferably from about 0.1 to about 100 reactor volumes/min. It has been found that the yield on TFE and/or HFP can be increased if the retention time of the fluorinated material in the decomposition zone is very short, which can be achieved, for example in fluidized bed reactors or in reactors using gas streams to carry the fluorinated material through the decomposition zone in short time. Preferred retention times are greater than 0 seconds and less than 60 seconds. Short retention times can be achieved by high flow rates of the respective gas streams. The processes may be run at a pressure of from about 0.01 bar to about 5 bar or at atmospheric pressure (1 bar). Preferably, the gas stream, for example carrier gas streams or fluidising gas streams have been pre-heated prior to introduction into the decomposition zone. Pre-heating is preferably carried out to temperature equal to the decomposition temperature or temperatures 50 to 200° C. below the decomposition temperature.

The fluorinated materials are subjected in the reactor to temperatures effective for the decomposition into fluoroolefins. The zone of the reactor where conditions are achieved under which decomposition takes place is referred to herein as "decomposition zone" of the reactor. Typically, such temperatures are from about 450° C. to about 900° C., preferably from about 550 to about 700° C. Optimum temperatures depend on the composition of the fluorinated material, the pressure under which the reactor is operated and the flow rate by which the fluorinated material is fed through the reactor and the rate at which the fluorinated material remains in the decomposition zone.

The decomposition temperatures may be generated entirely or in part by microwave irradiation (for example by a combination of microwave heating and conventional heating such as heating generated by heat exchange or combustion, or resistance heating. Therefore, the reactor comprises one or more microwave generators for generating microwave irradiation. Microwave-generated reactors are known in the art. The microwaves may be generated by devices known in the art including, for example, diodes, magnetrons, gyrotrons, travelling wave tubes, klystrons, ubitrons, amplitrons etc. Typically, the microwave generators are situated in the inside of the reactor. The inside of the reactor may be made of a material or coated with a material that increases the heating effect of the microwaves.

Microwave irradiation as referred to herein means irradiation with electromagnetic waves having a wave length of about 30 cm to about 3 mm and/or a frequency band of from about 300 MHz to about 300 GHz, preferably from about 915 MHz to about 2.45 GHz.

In a particular embodiment, the fluorinated material is subjected to microwave irradiation in the presence of microwave active particles. Typically this is realised by contacting the fluorinated materials with the particles while or immediately before the material is thermally decomposed. Typically, the particles are present in the reaction medium, for example by feeding the particles into the decomposition zone for example by a carrier gas stream or the particles may be present in the reaction medium, for example in the fluidised bed of a fluidised bed reactor.

Microwave active particles heat up upon irradiation by microwaves, for example through absorbtion of microwaves. Typically, microwave active materials heat up by at least 10° C. preferably by at least 20° C. and more preferably by at least 30° C. when submitting 1 g of the microactive material at ambient conditions to microwave irradiation of 0.7 kW for 5 minutes.

Preferably, the microwave active particles are solid at the decomposition temperature of the fluorinated material. Preferably, the microwave active particles have a melting point or decomposition point of greater than 800° C. or greater than 1,000° C. or even greater than 1,500° C.

Microwave active particles include particles comprising for example, but are not limited to, carbon, graphite, carbides, silicides, borides, nitrides, metal oxides, metal hydroxides, metal halides, in particular metal chlorides, metal fluorides, silicium carbide, boron carbides, titanium carbides, zirconium carbides, molebdenium silicides, titanium borides, sodium chloride, magnesium chlorides, potassium chloride, cobalt fluorides, potassium fluoride, calcium fluorides etc including mixtures and combinations thereof.

Further microwave active particles also include particles comprising metals, such as, for example, Ni, Pt, Co; Pt, metal alloys such as, for example, Pt/Cu, Pt/Re alloys, chromates, titanates and combinations or mixtures thereof.

The microwave active particles are preferably chosen such that they do not react with the reaction mixture and lose their microwave activity.

The microwave active particles may be used as combinations or blends of different microwave active particles.

The optimum size and amounts of the particles may be adapted to the specific composition of the fluorinated materials and the configuration of the reactor and the conditions at which the process is run. Typically, the particles have an average particle size (number average) of from about 100 µm to about 5 mm, preferably from about 250 µm to about 2 mm. The particles may be spherical or non-spherical. In case of spherical or substantially spherical particles the average size is determined by measuring the average diameter. In case of non-spherical, such as, for example, needle-like particles, the longest dimension (here the length) will be used for determining the particle size.

The amount ratio of microwave active particles to fluorinated material to be decomposed depends on the reactor type, dimension and configuration. Typically, the weight ratio of microwave active particles to material to be decomposed is from about 1:1,000 to about 1:0.1; preferably from about 1:10 to about 1:1.

Some of the microwave particles may be removed from the reactor, for example by the carrier gas stream, and may have to be replaced. This can be done by continuous, discontinuous feeding.

The microwave active particles may, for example, be present in the carrier gas or reaction medium or fluidised bed. This means the microwave active particles are in a mobile phase during the decomposition reaction. They may be introduced into the reactor through auxiliary gas streams simultaneously or non-simultaneously with the fluorinated material, or they may be present in the reactor before the fluorinated material is introduced into reactor. The microwave active particles may also be added to the fluorinated material for example before, during or after the fluorinated material is fed into the reactor, or more specifically into the decomposition zone. Alternatively, the microwave-active particles may also be present in an immobile phase during the decomposition reaction, for example, in the same or similar way as catalytic beds.

The presence of microwave active particles in the decomposition zone of the reactor generates hot spots in the reaction mixture facilitating heat transfer from the reactor to the reaction mixture. This can lead to a faster heat transfer into the reaction mixture and/or a more homogeneous distribution of heat within the reaction mixture compared to reactors that are not heated by microwave irradiation, such as reactors heated through heat exchange, combustion or electrical resistance. The presence of microwave active particles may also allow the process to be run more energy efficiently. It also allows for clearing more easily blocked reactors, for example caused by unreacted or polymerized material through overfeeding, by the collapse of fluidised bed and/or as a consequence of interrupting or terminating the decomposition reaction and/or shutting down the reactor.

The reactor may contain or may be connected to a plasma zone, where a plasma is generated. The plasma zone is typically located at, after the decomposition zone. The plasma may accelerate the decomposition reaction. When used after the decomposition zone the plasma may prevent or reduce precipitation of fluorocarbon particles and repolymerization. A plasma involves the ionisation of a gas. Inside the plasma negatively and positively charged compounds are present in substantially equal amounts. A plasma may be generated, for example through, microwave irradiation, for example by increasing the energy of the microwave irradiation until a plasma state is reached and stabilized. A plasma may also be generated, for example, by electric arcs, such as described, for example, in international patent application WO 01/58840 to Van der Walt et al, incorporated herein by reference, or, for example, by corona treatment.

The energy level of the plasma zone has to be optimized to stabilize the plasma but to prevent or reduce the deposition of fluorocarbon particles by minimizing the decomposition of fluoroolefins. The energy level required to generate and stabilize the plasma may depend on the composition and amounts of the product gas and if present carrier gas or gaseous reaction media.

The reactor may also contain or may be connected to a quenching zone. The quenching zone is located after the decomposition zone, and if a plasma zone is located after the decomposition zone, the quenching zone is typically located after that plasma zone. The hot product gas, generated by the decomposition of the fluorinated material and containing the fluoroolefins is quenched to stabilize the newly formed fluorocarbons and preventing or reducing repolymerization of the fluoroolefins. Therefore, the reactor itself may contain or it may be connected to a separate quenching zone, where the product gas is rapidly cooled. Typically quenching involves cooling the gas from a temperature of greater than 400° C., typically from about 400° C. to about 1,000° C., to a temperature below 250° C. in less than 5 seconds, preferably less than 1 second. Any suitable quenching system may be used, for example but not limited to expansion of the product gas, gas quenching by means of another gas which is cold, quench probes, for example those described in international patent application WO 01/58840 to Van der Walt, which is incorporated herein by reference, or a combination thereof.

A spread of fluorocarbons and non-fluorinated carbons may form as products from the decomposition reaction and may be present in the product gas. The desired fluoroolefins, in particular TFE and/or HFP may be separated by conventional gas separation systems, for example, condensation, expansion and distillation. Therefore, the process may additionally comprise separating TFE and/or HFP from the product gas.

The decomposition processes described herein may be run as batch process or they may be run continuously.

An embodiment of the process will now be described in detail by way of examples to further illustrate the invention. It is to be understood that the invention is not to be limited to the specific embodiment illustrated in the examples.

EXAMPLES

The fluorinated materials were continuously fed into a vertical fluidised bed reactor by a screw extruder and injected into the reactor by an argon stream. The inlet was situated at the bottom of the reactor. The reactor was a quartz tube containing two microwave horns located at about ⅓ and about ⅔ of the height of the reactor (height of the reactor was 576 mm and the diameter of the reactor was 346 mm). The microwave horns were placed at an angle of 90° C. with respect to each other.

The fluidised bed was generated in the reactor by feeding into the reactor a hot fluidising gas (a mixture of Ar and steam). The fluidised bed contained SiC particles as microwave active particles. At the top of the reactor was an outlet having a diameter of 54 mm leading product gas into a quencher, where the product gas was quenched with aqueous KOH at 4 bar.

The volume stream of the aq. KOH was adjusted such that the quenching temperature was about 40° C. The product mixture was analysed by gas chromatography for its composition and TFE content.

The process conditions for three different fluorinated materials and yields on TFE are summarised in table 1

TABLE 1

| | Example 1 | Example 2 | Example 3 |
|---|---|---|---|
| Fluorinated material | PTFE | PFA | FEP |
| Feed (g/min) | 2.8 | 1.2 | 2.5 |
| Feed Ar jet (Sl/min) | 3 | 3.5 | 3 |
| Temperature Ar jet | 15° C. | 15° C. | 15° C. |
| Fluidisation gas | Ar:steam | Ar:steam | Ar:steam |
| (Sl/min) | 1.5-3:3.5 | 5:0 | 2-3:2.8 |
| P Microwave (kW) 2.45 GHz maximum frequency) | 1.9-2.4 | 1.5-1.9 | 1.8-1.9 |
| pH KOH quenching | 12.5 | 12.5 | 12.5 |
| Temperature in quencher (° C.) | 23 | 20 | 25 |
| Temperature in reactor (° C.) | 650 | 620 | 700 |
| Temperature fluidisation gas (° C.) | 430-470 | 400 | 450-500 |
| Yield of TFE (%) | 76 | 87 | 77 |

Sl/min = standard liter per minute = 1 SL/min corresponds to 1.68875 (Pa × m³)/s

The invention claimed is:

1. Process for producing fluorinated olefins from a fluorinated material, the process comprising thermally decomposing the fluorinated material into fluoroolefins in the presence of microwave irradiation and in the presence of a carrier gas or a gaseous fluidised bed, wherein the fluorinated material is thermally decomposed at a temperature of from 550° C. to 700° C., further wherein the fluorinated material is thermally decomposed in a fluidized bed reactor while being contacted by microwave particles.

2. The process of claim 1 wherein the microwave active particles have a melting point of greater than 800° C.

3. The process of claim 1 wherein the microwave active particles comprise at least one component selected from silicides, carbides, borides, nitrides or a combination thereof.

4. The process of claim 1 wherein the decomposition is carried out in the presence of a carrier gas or a gaseous fluidised bed wherein the gas is selected from nitrogen, steam, a noble gas or a combination thereof.

5. The process of claim 1 wherein the microwave active particles are present in a carrier gas or a gaseous fluidised bed.

6. The process of claim 1 wherein the fluoroolefins comprise tetrafluoroethylene and/or hexafluorpropylene.

7. The process of claim 1 wherein the fluorinated material includes fluoropolymers, fluoropolymer containing compositions, liquid or gaseous fluorinated organic compounds having a molecular weight of less than 1000 g/mol of low molecular weight or combinations thereof.

8. The process of claim 1 wherein the process further comprises subjecting a product gas obtained by the thermal decomposition of the fluorinated material to a plasma treatment.

9. A process of generating tetrafluoroethylene comprising
  (i) fluorinating hydrocarbons to generate fluorinated hydrocarbons
  (ii) subjecting the fluorinated hydrocarbons to a thermal decomposition process according to.

* * * * *

UNITED STATES PATENT AND TRADEMARK OFFICE
CERTIFICATE OF CORRECTION

PATENT NO. : 8,344,190 B2
APPLICATION NO. : 13/121297
DATED : January 1, 2013
INVENTOR(S) : Klaus Hintzer It is certified that error appears in the above-identified patent and that said Letters Patent is hereby corrected as shown below:

In the Specifications:

Column 1
Line 9, Delete "Sep. 20, 2009," and insert -- Sep. 30, 2009, --, therefor.
Line 17, Delete "fluoroolefines," and insert -- fluoroolefins, --, therefor.

Column 2-3
Line 57-67, Delete "The Compounds.......mixtures thereof." and insert the same on Col. 2, Line 58 as a new paragraph.

Column 6
Line 18, Delete "molebdenium" and insert -- molybdenum --, therefor.

In the Claims:

Column 9
Line 9, In Claim 6, delete "hexafluorpropylene." and insert -- hexafluoropropylene. --, therefor.

Column 10
Line 11, In Claim 9, delete "to." and insert -- to claim 1. --, therefor.

Signed and Sealed this
Sixteenth Day of April, 2013

Teresa Stanek Rea
*Acting Director of the United States Patent and Trademark Office*